US008455226B2

(12) United States Patent
De Windt et al.

(10) Patent No.: US 8,455,226 B2
(45) Date of Patent: Jun. 4, 2013

(54) METHOD FOR PRODUCING METAL NANOPARTICLES

(75) Inventors: Wim De Windt, Sint-Amandsberg (BE); Tom Vercauteren, Sint-Amandsberg (BE); Willy Verstraete, Wondelgem (BE)

(73) Assignee: Janssen Pharmaceutica N.V., Beerse (BE)

( * ) Notice: Subject to any disclaimer, the term of this patent is extended or adjusted under 35 U.S.C. 154(b) by 651 days.

(21) Appl. No.: 12/307,190

(22) PCT Filed: Jul. 5, 2007

(86) PCT No.: PCT/EP2007/006145
§ 371 (c)(1),
(2), (4) Date: May 14, 2009

(87) PCT Pub. No.: WO2008/003522
PCT Pub. Date: Jan. 10, 2008

(65) Prior Publication Data
US 2009/0239280 A1 Sep. 24, 2009

Related U.S. Application Data

(60) Provisional application No. 60/818,579, filed on Jul. 5, 2006.

(30) Foreign Application Priority Data

Nov. 30, 2006 (GB) .................................. 0623925.5

(51) Int. Cl.
*C12P 3/00* (2006.01)
(52) U.S. Cl.
USPC ......... 435/168; 435/170; 435/252.9; 424/618
(58) Field of Classification Search
None
See application file for complete search history.

(56) References Cited

U.S. PATENT DOCUMENTS

| 6,379,712 B1* | 4/2002 | Yan et al. ..................... 424/618 |
| 2002/0174743 A1 | 11/2002 | Mukherjee et al. |
| 2003/0004375 A1 | 1/2003 | Mizrahi et al. |
| 2005/0013759 A1 | 1/2005 | Grow |
| 2007/0207335 A1 | 9/2007 | Karandikar et al. |

FOREIGN PATENT DOCUMENTS

| DE | 10337399 A1 | 3/2005 |
| JP | 2004137241 | 5/2004 |
| WO | WO 0218699 | 3/2002 |

OTHER PUBLICATIONS

Kashefi, K., et al., "Reductive precipitation of gold by dissimilarity Fe(III)-reducing bacteria and archaea", *Applied and Environmental Microbiology*, Washington, D.C., 67(7), Jul. 2001, pp. 3275-3279.

Klaus, T., et al., "Silver-based crystalline nanoparticles, microbially fabricated", *Proceedings of the National Academy of Sciences of the United States of America*, 96(24), Nov. 23, 1999, pp. 13611-13614.
Mandal, D., et al., "The use of microorganisms for the formation of metal nanoparticles and their application", *Applied Microbiology and Biotechnology*, 69(5), Jan. 2006, pp. 485-492.
Merroun, et al., "Spectroscopic characterization of gold nanoparticles formed by cells and S-layer protein of *Bacillus sphaericus* JG-A12", *Materials Science and Engineering C, Elsevier Science S.A*, Ch., 27(1), Jun. 9, 2006, pp. 188-192.
Mukherjee, P., et al., "Bioreduction of AuCl(4)(−) ions by the fungus *Verticillium* sp. And surface trapping of the gold nanoparticles formed", *Angewandte Chemie. International Edition, Wiley VCH Verlag*, Weinheim, DE, 40(19), 2001, pp. 3585-3588.
Nair, B., et al., "Coalescence of nanoclusters of submicron crystallites assisted by *Lactobacillus* strains", *Crystal Growth & Design*, 2(4), 2002, pp. 293-298.
Pei, L., et al., "Synthesis of gold nanorods by surfactant-assisted one-step chemical reduction method", Abstracts 206th Meeting electrochemical society, 2004, Abstract No. 231.
Shahverdi, A.R., et al., "Rapid synthesis of silver nanoparticles using culture supernatants of enterobacteria: A novel biological approach", *Process Biochemistry*, 42(5), May 2007, pp. 919-923.
Silver, S., "Bacterial silver resistance:molecular biology and uses and misuses of silver compounds", *FEMS Microbiology Reviews*, 27, 2003, pp. 341-353.
Database WPI Week 200245 Derwent Publications Ltd., London, GB; AN 2002-425694, XP002453841, 2002.
Database WPI Week 200435 Derwent Publications Ltd., London, GB; AN 2004-369133; XP002453842, 2004.
European Patent Application No. 07765165.1, Office Action dated Feb. 28, 2011, 4 pages.
Japanese Patent Application No. 2007800251987, Office Action dated Apr. 11, 2010, 10 pages.
Lin et al., "A Further Insight Into The Mechanism of Ag+ Bisorption by *Lactobacillus* sp. Strain A09", Spectrochimica Acta Part A, Apr. 6, 2005, 6(61), 1195-1200.
Morones et al., "The Bacterial Effect of Silver Nanoparticles", Nanotechnology, Aug. 26, 2005, 2346-2353.
Russian Patent Application No. 2009103776, Office Action dated Jan. 28, 2011, 3 pages.
Sondi et al., "Silver Nanoparticles as Antimicrobial Agent: A Case Study on *E. coli* as a Model for Gram-Negative Bacteria", Journal of Colloid and Interface Science, Mar. 18, 2004, 177-182.

(Continued)

*Primary Examiner* — Susan Hoffman
(74) *Attorney, Agent, or Firm* — Woodcock Washburn LLP (57) ABSTRACT

This invention provides a method for producing a composition comprising colloidal nanoparticles of metals including silver, gold, zinc, mercury, copper, palladium, platinum, or bismuth, by contacting a metal or metal compound with bacteria. An embodiment of the method comprises a step of incubating probiotic bacteria with an aqueous solution comprising at least 4 mM of a silver or gold salt. A resulting nanosilver-containing composition is useful as a highly efficient antimicrobial agent, for instance when impregnated onto a carrier, or an algicide agent or a herbicide agent.

19 Claims, 4 Drawing Sheets

OTHER PUBLICATIONS

Chinese Patent Application No. 200780025198.7, Third Office Action dated Nov. 2, 2011, 5 pages (English Translation Included).

Australian Patent Application No. 2007271357, Office Action dated Nov. 18, 2011, 2 pages.

Russian Patent Application No. 2009103776, Office Action dated Aug. 18, 2011, 8 pages (English Translation Included).

Nair et al., "Coalescence of Nanoclusters and Formation of Submicron Crystallites Assisted by *Lactobacillus* Strains", Crystal Growth & Design, Jun. 2002, 2(4), 293-298.

Zheng-yi et al., "Optimization of C/N ratio for preparation of protein-rich and multi-enzymes feed thallus through synergic fermentation of mixed distillers' grains", Journal of Environmental Sciences (China), Jan. 2002, 14(1), 141-144.

Chinese Patent Application No. 200780025198.7: Chinese Fourth Office Action dated Mar. 20, 2012, 8 pages (Redacted).

Fu, et al, "Rapid Preparation Process of Silver Nanoparticles by Bioreduction and Their Characterizations," Chinese J. Chem. Eng., 2006, 14(1), 114-117.

Fu, et al, "Spectroscopic Characterization on the Biosorption and Bioreduction of Ag (I) by Lactobacillus sp. A09," Acta Physico-Chimica Sinica, Sep. 2000, 16(9), 770-782.

Fu, et al., "Characterization of Adsorption and Reduction of Noble Metal Ions by Bacteria," Chemical Journal of Chinese Universities, 1999, 20(9), 1452-1454.

Zhang, et al, "Biosorption and Bioreduction of Diamine Silver Complex by Corynebacterium," Journal of Chemical Technology and Biotechnology, 2005, 80, 285-290.

\* cited by examiner

METHOD FOR PRODUCING METAL NANOPARTICLES

CROSS-REFERENCE TO RELATED APPLICATIONS

This application is the U.S. National Stage of International Application No. PCT/EP2007/006145, filed Jul. 5, 2007, which claims priority to U.S. Application No. 60/818,579 filed Jul. 5, 2006 and to British Application No. 0623925.5 filed Nov. 30, 2006, the disclosures of which are incorporated herein by reference in their entirety.

FIELD OF THE INVENTION

The present invention relates to the production of colloidal metal compounds on a bacterial membrane. The present invention also relates to methods for producing silver or gold nanosize particles by means of a biological process. In particular the invention relates to the use of probiotic bacteria such as, but not limited to, *Lactobacillus* under specific conditions in the production of metallic nanoprecipitates, in particular silver or gold nanoparticles with a goal of improving their anti-microbial efficiency. This invention also relates to disinfecting products including a carrier impregnated with a composition comprising colloidal nanosilver or nanogold produced by said method.

BACKGROUND OF THE INVENTION

Effective disinfecting processes are necessary for the treatment of bulky amounts of polluted materials such as water, especially domestic and industrial circulating waters, and aqueous effluents (such as being present in the foodstuff processing industry) containing micro-organisms which cannot be discharged or re-used untreated for hygienic, operational or environmental reasons. Effective disinfecting processes are also necessary for treating surfaces such as premises, equipment, containers, air-conditioning systems and the like. Environmentally compatible disinfecting processes are mainly based on the use of active oxygen compounds, such as hydrogen peroxide, or monomeric quaternary ammonium compounds.

Hydrogen peroxide is a moderately active, mild disinfectant with bactericidal properties. Hydrogen peroxide concentrations of 25 mg/l are known to inhibit the growth of some bacteria, however an effective reduction of the germ count, even at a much higher hydrogen peroxide concentration, takes many hours or requires additional ultraviolet radiation. Generation of the latter, however, requires both expensive equipment and substantial electricity costs. Therefore when disinfecting large amounts of polluted materials such as water, for instance for the treatment of water in sewage works and their outputs, such measures are practically inadequate and/or uneconomic. Therefore, various ways to overcome these disadvantages have already been tried in the art.

It is well known in the art that silver ions and silver-based compounds are highly toxic to micro-organisms, therefore showing strong bactericidal effects in many common species of bacteria including Escherichia coli. It has also been showed that hybrids of silver nanoparticles with amphiphilic hyperbranched macromolecules exhibit effective antimicrobial surface coatings. Stable aqueous dispersions of silver nanoparticles in the form of non-toxic elementary silver hydrosols were found to be strongly bactericidal for *E. coli.*, a concentration of 50 µg/cm$^3$ causing 100% inhibition of bacterial growth. Silver nanoparticles were found to accumulate in the bacterial membranes, somehow interacting with certain building elements of the bacterial membrane, thus causing structural changes, degradation and finally, cell death. The surface of bacteria is overall reported to be negatively charged, at biological pH values, due to the dissociation of an excess number of carboxylic and other groups in the membrane. It has been suggested that silver nanoparticles embedded in the membrane carbon-matrix generate a surface charge due to their movement and friction inside the matrix and in this way electrostatic forces might be a cause for the interaction of the nanoparticles with the bacteria. Furthermore, silver will tend to have a higher affinity to react with phosphorous and sulphur compounds contained in the bacterial membrane but also in DNA. A third possible mode of action is the release of silver ions which may further contribute to the bactericidal effect of silver nanoparticles. Several species of micro-organisms, e.g. *Lactobacillus* sp. and the fungus *Fusarium oxysporum*, have been reported to biosorb Ag(I) to their cell surface and detoxify this ion by reduction to Ag(0), either by reductase action or by electron shuttle quinones or both.

A non cytotoxic antimicrobial formulation comprising biologically stabilized silver nanoparticles in the size range of 1 to 100 nm, and a carrier in which the concentration of the said biologically stabilized silver nanoparticles is in the range of 1 to 6 ppm is already known in the art.

It is also known a method for preparing a colloidal silver-biomolecule complex comprising:
  providing a mixture of a biomolecule, a silver salt, and a source of halide ions in a single solution; and
  irradiating the mixture with light having a wavelength in the visible region, wherein the silver salt and source of halide ions are water soluble; the amounts of the biomolecule, the silver salt and the source of halide ions being such that, the irradiating step results in formation of colloidal silver-bio-molecule complexes.

It has also been disclosed a process for the preparation of nano-sized colloidal metal particles, said process comprising treating wet fungus or fungus extract with a metal ion solution at a temperature in the range of 15 to 40° C. for a time period ranging between 2 to 120 hours, and separating the biomass to obtain the nano-sized colloidal metal particles.

Conventional production methods for making silver nanoparticles have a number of disadvantages such as high production costs, the production of a significant proportion of by-products, or the existence of an upper limit for the concentration of nanoparticles obtained. For instance the latter production method requires a significantly high production time and is based on using fungus that may be pathogenic. Therefore there is a need in the art for a method for making silver nanoparticles that is reliable, inexpensive and reduces or avoids the formation of by-products.

An Ag(I) biosorption process by means of *Lactobacillus*, its pH dependency in the pH range from 2 to 6 and temperature dependency in the range from 10 to 60° C., as well as the mechanism of the reduction of Ag$^+$ to Ag by *Lactobacillus*, has also been studied.

It is also known in the art a process for preparing silver nanoparticles by bioreduction using *Aeromonas* sp. in admixture with silver ions, ammonia and sodium hydroxide, at 60° C. during a couple of hours.

The above mentioned processes suffer from disadvantages like the elevated temperature, acidic pH and/or high incubation time required, or the insufficient bactericidal activity of the silver nano-particles resulting therefrom.

There is therefore a need in the art for producing silver or gold nanoparticles by a method which is free from these disadvantages.

There is also a need in the art for a simple, environmentally-friendly and reproducible method for producing silver or gold nanoparticles with high anti-microbial properties.

There is also a need in the art for a corresponding method for producing gold or silver nanoparticles which are known to be useful in certain medical applications.

Colloidal forms of metals other than gold or silver, and compounds of said metals, are also known in the art to have valuable properties and applications. For instance, colloidal bismuth subcitrate is water-soluble especially at a pH range from about 3 to 8 and has been used for decades for the treatment of gastric and duodenal ulcers, and *Helicobacter pylori* infection together with antibiotics. Colloidal forms of mercury, inorganic mercury compounds and metallic mercury ointments have been used topically for a variety of therapeutic uses including the treatment of infected eczema or impetigo (mercury salts), the treatment of syphilis (calomel), the treatment of psoriasis (mercuric oxide or ammoniated mercury). Colloidal forms of palladium and platinum have been used as catalysts for a variety of chemical reactions including organic reductions, hydrogenolysis and the like. Platinum nanoparticles in colloidal form are also known as anti-cancer agents. Colloidal copper, optionally chelated with salicylic acid, is a strong anti-inflammatory agent, and sublingual forms of colloidal copper or colloidal zinc are known as being active for fighting colds and flu. Also, colloidal zinc can be especially effective against viruses. In all these various fields there is a permanent need for providing alternative physical forms of the colloidal metals or colloidal metal compounds in order to improve their efficiency in their relevant fields of application.

SUMMARY OF THE INVENTION

In its broadest expression, the present invention relates to the use of bacteria for the production of colloidal metal compounds on the bacterial membrane and the subsequent use of the coated bacteria as an antimicrobial agent. In particular the invention relates to:
  The use of bacteria for the production of colloidal metal compounds by contacting the said bacteria with a mixture of metal salts and other salts, under a controlled pH making the bacteria to produce colloidal metal compounds on its membrane, and
  The use of the above mentioned bacteria coated with the metal compounds on the membrane as an antimicrobial agent.

In one embodiment the invention relates to the production of metallic nanoprecipitates by probiotic and other bacteria that can be used as an antimicrobial agent in drinking water, in surface coatings and other materials.

More specifically some bacteria can reduce Ag(I) salts to colloidal Ag(O) that precipitates as nano-Ag particles on the cell surface. The biomass coated with colloidal silver or other metallic nanoprecipitate can easily be harvested from a water phase by filtration or centrifugation, can be washed and rinsed and further processed, and provides a colloidal product with strong antimicrobial properties, both in (diluted) suspension and when processed in coatings.

Interestingly a series of probiotic bacteria, i.e. bacteria that are produced industrially for their beneficial effects on human health when they are present into the human digestive tract, demonstrate this ability to produce Ag nanoprecipitates on their cell surface. These bacteria include, but are not limited to, probiotic *Lactobacillus fermentum* strains.

By adding a specific combination of salts ($AgNO_3$, $NH_4Cl$, NaOH and others) to a concentrated cell culture of bacteria and controlling the pH, a colloidal-silver product is formed with strong anti-microbial properties, Other metal salts combined with certain bacterial strains results in nanoprecipitates with similar properties, and this is also part of this invention.

By adjusting the ratio of "mass-of-silver" to "mass-of-biological-cells" (Ag:CDW, with CDW=cell dry weight), the reactivity and properties of the final colloidal silver product can be varied, in terms of colloidal particle size, colloidal particle distribution and other properties thereof.

The colloidal silver compounds produced on the surface of the bacteria have a very broad range of applications, consisting of but not limited to: water disinfection, use as disinfecting agent in cleaning products, as cleaning agent, formulation in antimicrobial coatings, medical applications, human consumption, use in textile, application in ointments and lubricants, as a catalyst, etc.

The production process is straightforward, cost efficient, has a high yield and can easily be upscaled, the size and distribution of the particles can be controlled and the antimicrobial reactivity of the nanosilver produced outperforms other colloidal silver products at very low (ppb) concentrations. Moreover, the product can be processed under different forms: dried, in suspended form or as "wet" pellet, it can be formulated into different applications. No residues of chemical reagents are present in the final product, since it can be rinsed with pure water without loss of activity.

The use of probiotic bacteria opens up many applications in health care and food industry. The Ag coated bacteria product would be especially suited for the following applications:
  Formulation in disinfecting cleaning products (hospitals, laboratories, animal production grounds, and others)
  Application in ceramic filters or other filters for water disinfection, both drinking water, swimming pool water, animal production water, aquaculture breeding water, any many others
  Application in disinfecting coatings: polymers, textile fibers, metals,
  Suitable for formulation in disinfecting skin ointments, lubricants, etc,
  Applications to disinfect drinking water: development countries, backpackers, airplanes, and many others (easy-drop method), and
  Combatting pathogens: *Legionella, Cryptosporidium*, Hepatitis, Herpes, *Pseudomonas, Staphylococcus*, different types of bacteria, fungi and viruses.

One object of the present invention is to provide gold or silver nanoparticles of good quality. It is a first aspect of the present invention to provide an improved biological method for producing a composition comprising colloidal silver or gold nanoparticles, said method comprising the use of probiotic bacteria, in particular a *Lactobacillus* species such as Lactobacillus fermentum, and contacting said biomass with an aqueous solution of a silver (I) salt or a gold (III) salt. The present invention is based on the unexpected finding that certain specific process parameters for producing silver or gold nanoparticles by bioreduction greatly affect the production efficiency and the characteristics of the resulting nanoparticles. In particular the specific methods of the present invention greatly affect the antimicrobial activity of a resulting composition comprising silver nanoparticles.

It is another aspect of the present invention that the silver or gold nanoparticles composition obtained by bioreduction under these specific conditions may be further processed, e.g.

separated from the biomass, while maintaining or even further improving their activity or other relevant properties such as stability over storage. Alternatively a chemical post-treatment, e.g. by means of an oxidising species such as a peroxide or a per-salt, of a gold or silver nanoparticle composition obtained by bioreduction under these specific conditions may even enhance the properties of the resulting nanoparticle composition.

It is also an advantage of the process of the present invention that the size and distribution of the resulting silver or gold nanoparticles can be controlled in a reproducible way.

It is also an advantage of the present invention that said method achieves a highly reliable result within a significantly short time, at low expense and in an environmentally-friendly way, by reducing the need for potentially toxic and/or expensive chemicals. No harmful residues of chemical reagents are left in the composition resulting from the method of the invention, to a large extent since the biomass used originates from a harmless, for instance probiotic, micro-organism. It is therefore an advantage of the present invention that the method provides a composition that upon application with eukaryotic organisms, does not substantially affect such organisms. In a specific embodiment, the invention provides a composition with high anti-microbial activity that also works against marine pathogens, without substantially affecting eukaryotic organisms. It is an additional advantage of the invention that the invention allows the production of a composition comprising nanosilver or nanogold in high concentration as such, and comprising nanosilver or nanogold composed substantially by silver or gold in their metallic state respectively, for example comprising more than about 95% of $Ag^0$ on the total silver content or more than about 95% of $Au^0$ on the total gold content respectively.

It is another advantage of the present invention that the resulting product or composition can easily and safely be processed while maintaining or even improving its activity. The composition can be dried, or maintained in suspended form or as a wet pellet, and it can be formulated under different forms, such as aerosol formulations or impregnation onto a carrier, without affecting the anti-microbiological activity due to the stability of the nanosilver particles.

In yet another embodiment, the present invention relates to the use of a colloidal silver composition produced according to the above-mentioned method as an algicide or herbicidal agent.

Definitions

The terms "nanosilver" or "nano-Ag" as used herein for the purpose of the present invention refer to nanoparticles of metallic silver ($Ag^0$). Within the meaning of the present invention, said nanoparticles may or may not be deposited onto a biomass. These nanoparticles may vary in size between about 0.1 nm and about 100 nm, for example within a range from about 0.5 nm to about 5 nm. These nanoparticles may also vary in size distribution around their average size.

The terms "nanogold" or "nano-Au" as used herein for the purpose of the present invention refer to nanoparticles of metallic gold ($Au^0$). Within the meaning of the present invention, said nanoparticles may or may not be deposited onto a biomass. The nanoparticles may vary in size between about 0.1 and about 100 nm, for example within a range from about 0.5 to about 5 nm.

The term "biomass" as used herein for the purpose of the present invention refers to the organic material consisting of, or derived from, the bacterial species used for producing "nanosilver" or "nanogold".

The term "probiotic bacteria" as used herein for the purpose of the present invention refers to bacteria that when administered in adequate amounts to a host such as a mammal, a marine species (e.g. a fish) or a human being, confer a beneficial effect on the health of said host.

The term "silver (I)" or "Ag (I)" as used herein for the purpose of the present invention refers to monovalent positively charged silver ions or $Ag^+$.

The terms "gold (I)" and "gold (III)" as used herein for the purpose of the present invention refers to monovalent and trivalent positively charged gold ions respectively.

DETAILED DESCRIPTION OF THE INVENTION

It is a first aspect of the present invention to provide a simple method for producing a composition comprising colloidal nanosilver or nanogold comprising a step of incubating probiotic bacteria with an aqueous solution comprising at least 4 mM of a silver or gold salt.

According to the present invention, suitable probiotic bacteria include genera such as, but not limited to, *Lactobacillus, Bifidobacterium, Escherichia, Enterococcus, Saccharomyces* and *Bacillus*. Without limitation, the probiotic bacteria may belong to one or more of the following species: *Lactobacillus sakei, Lactobacillus acidophilus, Lactobacillus casei, Lactobacillus cripatus, Lactobacillus delbrueckii* subspecies *bulgaricus, Lactobacillus fermentum, Lactobacillus gasseri, Lactobacillus johnsonii, Lactobacillus paracasei, Lactobacillus plantarum, Lactobacillus reuteri, Lactobacillus rhamnosus, Bifidobacterium bifidum, Bifidobacterium breve, Bifidobacterium infantis, Bifidobacterium longum, Bifidobacterium lactis, Bifidobacterium adolescentis, Escherichia coli* Nissle, *Saccharomyces boulardii, Streptococcus thermophilus, Enterococcus faecium, Bacillus licheniformis, Bacillus cereus, Bacillus subtilis, Bacillus megaterium, Bacillus acidophilus, Bacillus pumilus, Bacillus polyfermenticus, Bacillus clausii, Bacillus laterosporus, Bacillus sporogenes, Bacillus coagulas,* and *Bacillus polymyxa*.

For the purpose of the various embodiments of the method of the present invention, any water soluble silver salt may be used. As used herein, the term "silver salt" also encompasses hydrates and other solvates of such silver salts. Typically, a water soluble silver salt may be defined herein as a silver salt with a water solubility of at least 0.1 g/L at the temperature of performance of the method of this invention, e.g. at room temperature. Without limitation, the silver salt may be an inorganic silver salt or an organic silver salt such as, but not limited to, silver acetate, silver chloride, silver perchlorate, silver chlorate, silver bromide, silver fluoride, silver lactate, silver nitrate, silver sulfate or silver tartrate.

For the purpose of the various embodiments of the method of the present invention, any water soluble gold salt may be used. As used herein, the term "gold salt" also encompasses hydrates and other solvates of such gold salts. Typically, a water soluble gold salt is a gold salt with a water solubility of at least 0.1 g/L at the temperature of performance of the method of this invention, e.g. at room temperature. Without limitation, the gold salt may be monovalent or trivalent. Without limitation, the gold salt may be an inorganic gold salt or an organic gold salt or a mixed gold salt such as, but not limited to, gold (III) chloride, gold sodium thiomalate monohydrate, gold (III) bromide, gold (III) iodide and gold (III) nitrate.

According to an embodiment of the present invention, the initial concentration of silver or gold salt in the aqueous solution to be incubated should be at least 4 mM, for instance at least 10 mM, or as a particular example at least 50 mM.

According to another embodiment of the present invention, said aqueous solution may further comprise additional components that are susceptible to influence the behavior, in particular improve the properties of the resulting composition. In this respect, in an embodiment of the present invention wherein nanosilver is desired, the method may comprise a step of incubating probiotic bacteria (such as defined herein before) with an aqueous solution comprising at least 4 mM of a silver salt and further comprising ammonia and/or an ammonium salt. Ammonium salts suitable for this embodiment are such as, but not limited to, ammonium chloride, ammonium nitrate, ammonium phosphate, ammonium sulfate, ammonium carbonate, ammonium formate and ammonium bromide. The amount of ammonia and/or ammonium salt used in this embodiment of the invention should preferably be sufficient to allow for the formation of a substantial amount of a silver-ammonia or silver-ammonium complex such as, but not limited to, a silver(I)-ammonia complex under the form of $Ag(NH_2)^+$ and/or $\{Ag(NH_3)_2\}^+$. According to another variant of this embodiment of the present invention, the aqueous solution to be incubated may further comprise a suitable amount of an alkali metal hydroxide such as, but not limited to, sodium hydroxide or potassium hydroxide. Such a suitable amount may be defined by reference to a suitable pH range to be achieved, as explained herein below. According to another embodiment of the present invention, the method comprises a step of incubating probiotic bacteria (such as defined herein before) with an aqueous solution comprising at least 4 mM of a gold salt and further comprising a suitable amount of an alkali metal hydroxide such as, but not limited to, sodium hydroxide or potassium hydroxide in the absence of ammonia and/or an ammonium salt. Suitable alkali metal hydroxides such as, but not limited to, sodium hydroxide and/or potassium hydroxide may be added to the incubating aqueous solution in concentrations up to about 1M. Preferably, incubation is performed under conditions such that the pH is at least 8, for example within a range from about 8 to about 12, or as a more specific embodiment within a range from about 8.5 to about 11.

According to an embodiment of the present invention, the ratio of silver weight or gold weight to cell dry weight (hereinafter abbreviated as CDW) of the probiotic bacteria is at least about 0.01, for example at least about 0.05 or at least about 0.1.

According to another embodiment of the present invention the Ag:CDW or Au/CDW weight ratio is not above about 20, preferably below about 10, for example below 5.

According to an embodiment of the present invention, the incubation step of the method is performed at a temperature from about 5° C. to about 45° C., preferably at a temperature from about 15° C. to about 35° C., for example at room temperature.

As another embodiment of the present invention, the incubation step of the method may be carried out during a period of time from about 1 second to about 30 minutes, for instance from about 5 seconds to about 20 minutes. The skilled person is able to determine with limited experimentation the most appropriate period of time for incubation, depending upon other process parameters such as, but not limited to, the concentration of silver or gold salt, the temperature of incubation, the Ag:CDW or Au/CDW weight ratio, the presence or absence of ammonia or an ammonium salt, and the like. As is conventional in the art, incubation may be carried out under agitation during at least part of the incubation time.

The method of the present invention may also comprise a step of further processing of the resulting composition comprising colloidal silver or gold nanoparticles. Said further processing may comprise one or more steps such as, but not limited to, the removal of at least part of the biomass from the silver or gold nanoparticles or fractionation of the biomass by means of mechanical, enzymatic and/or physicochemical treatment, e.g. by sonication. Each of such biomass removal or fractionation methods is well known to those skilled in the art. Alternatively or in addition, said processing may include a chemical treatment step for stabilizing or even improving certain desirable properties of the resulting composition comprising colloidal silver or gold nanoparticles. As a particular embodiment of such chemical processing, a gold or silver nanoparticle composition according to the present invention may be treated after incubation, and optionally biomass removal, with an oxidising agent such as a peroxide or a per-salt in order to yield a silver or gold nanoparticle precipitate with an improved stability and/or (with respect to nanosilver) with a higher antimicrobial activity. Within this embodiment of the present invention, suitable organic and inorganic peroxides include, but are not limited to, hydrogen peroxide, peracetic acid and the like. Suitable per-salts for use in this embodiment of the present invention include, but are not limited to, alkaline water-soluble salts being able to form hydrogen peroxide upon dissociation, e.g. when such salts are dissolved in water, a peroxide ion is released. Suitable examples thereof include percarbonates, perborates, persilicates and perphosphates associated with a cation such as an alkali metal. Especially preferred is sodium percarbonate having the empirical formula $2Na_2CO_3, 3 H_2O_2$. In support to this embodiment of the present invention, the skilled person knows that:

such per-salts may be superior to hydrogen peroxide with regard to disinfection capacity, hydrogen peroxide is a weak disinfectant and has poor permeability into bacteria, and when a per-salt is dissolved in water and liberates hydrogen peroxide, the alkaline salt extracts a proton from the liberated hydrogen peroxide forming the hydroperoxide ion which, in contrast to hydrogen peroxide, is a strong disinfectant and is readily permeably into bacteria.

At any time of the process of the invention, the solid portion comprising the colloidal nanosilver or nanogold can be separated from the liquid portion in any manner well known to the skilled person. For instance, it may be separated by centrifugation and subsequent decantation of the liquid fraction, or by filtration.

In the method of the present invention, a silver or gold salt may be at least partly replaced with a copper salt while carefully adjusting one or more of the reaction operational conditions such as, but not limited to, pH, incubation temperature, type of salt and salt concentration. In the method of the present invention, probiotic bacterial species may also be at least partly replaced with alternative micro-organisms or bacteria while carefully adjusting one or more reaction operational conditions such as, but not limited to, pH, incubation temperature, type of salt, and (gold or silver) salt concentration. Such alternative bacteria may be selected from the group consisting of bacteria being generally regarded as safe to the environment, more specifically those bacteria known to have bioreductive capacity.

Although the method of the present invention has been mainly described herein with respect to silver and gold, it is not limited thereto but as mentioned in its broadest expression it is also applicable to other metals or metal compounds, provided that one or more reaction operational conditions such as, but not limited to, pH, incubation temperature, type of salt, and salt concentration are suitably adapted. Such adaptation is within the scope of routine experimentation for the skilled person, given the general teachings incorporated herein. Metals of special interest within the scope of this invention include zinc, mercury, copper, palladium, platinum, and bismuth.

A second aspect of the present invention is an antimicrobial use of a nanosilver composition produced by the above described method, based on the unexpected finding that an effective concentration of such nanosilver composition in an antimicrobial treatment may be exceptionally low, depending upon the targeted bacteria, e.g. about 0.5 ppm or even lower, for example about 0.05 ppm or lower, and on the finding that a substantial decrease in the amount of undesirable bacteria may be observed within a limited period of time, e.g. within no more than about 5 hours. Suitable bacterial targets for this aspect of the present invention include a wide range of gram-positive and gram-negative germs such as, but not limited to, *Pseudomonas aeruginosa* (e.g. CMCM-2-22 strain), *Pseudomonas cepacia, Enterobacter cloacae, Enterobacter agglomerans, Klebsiella pneumoniae* (e.g. ATCC-10031 strain), *Eschericia coli, Streptococcus faecalis* (e.g. ATCC-10541 strain), *Staphylococcus cohnii, Staphylococcus aureus* (e.g. IP 52154 or ATCC-6538 strain), *Bacillus subtilis* (ATCC-19659 strain) (all being customary to hospital bacterial strains), *Enterococcus facium, Enterococcus hirae, Thiobacillus ferrooxidans* (e.g. ATCC 13661 strain), *Lactobacilli, Thermophilic bacilli, Trychophyton interdigitale* (e.g. ATCC-640 strain), *Clostridium sporogenes* (ATCC-3584 strain), *Clostridium perfringens* (ATCC-13124 strain), *Salmonella typhimurium, Listeria monocytogenes* and the like. The nanosilver composition of this invention may also be active against fungi, including for instance *Candida albicans* (e.g. APCC-2091 strain) *Mycobacterium smegmatis* (e.g. IP 7326 strain), *Aspergillus niger* (e.g. 218 IP strain), *Penicillium verrucosum* and the like, and may also have antiparasitic activity against for instance *Schistosoma haematobium, Schistosoma mansoni* and the like.

The antimicrobial (or antifungal or antiparasitic or antiviral) use may, according to a particular embodiment of the present invention, be in the form of a liquid disinfecting composition wherein a nanosilver composition produced by the above described methods may be combined with a second anti-microbial agent or a mixture of such agents. Suitable examples of a second anti-microbial agent include, but are not limited to, hydrogen peroxide, quaternary ammonium salts, peracetic acid, per-salts (the latter being as described herein above with respect to the first aspect of the present invention), and mixtures thereof in any known proportions. In particular, said combination may provide synergistic effects in antimicrobial activity. In a specific embodiment, said second anti-microbial agent may be an oxidising antimicrobial agent such as, but not limited to, chlorine dioxide, monochloramine, a hypochlorite, potassium permanganate, iodine or chlorine. The liquid disinfecting compositions according to this embodiment of the invention may further include one or more stabilizers, such as for instance phosphoric acid, nitric acid, sulfuric acid, hydrobromic acid or boric acid or mixtures thereof, namely for the purpose of adjusting the pH of the composition within a range suitable for handling and use. Among inorganic acid stabilizers, phosphoric acid is especially preferred. In practice, the said acid stabilizer may commonly already be incorporated in a suitable amount into a commercially available hydrogen peroxide grade. The stabilizer optionally used in this invention may also be an organic carboxylic acid such as tartaric acid, citric acid (or a hydrate thereof), benzoic acid, picolinic acid, nicotinic acid and isonicotinic acid. Mixtures of inorganic and organic acids may be considered as well for this purpose. The said stabilizer(s), when present, are preferably in an amount effective for pH adjustment and/or long-term storage stability of the liquid disinfecting composition. These disinfecting liquid compositions of this invention may also include at least one component selected from the group consisting of surfactants, corrosion inhibitors and fragrances (perfumes).

Suitable surfactants for use in the disinfecting compositions of the present invention include for instance, but are not limited to, cationic, non-ionic, amphoteric and zwitterionic surface-active compounds, preferably those suitable for contact with foodstuffs or drinking water at the relevant dose, and mixtures of such compounds. A wide variety of non-ionic surfactants are potentially useful herein. Non-limiting examples of anionic surfactants include, for instance, those selected from the group consisting of polyethoxylated and/or polypropoxylated glycols, $C_8$-$C_{20}$ fatty acid monoesters, sorbitan monopalmitate and the like. Specific examples of suitable amphoteric surfactants include sodium 3-dodecylaminopropionate, sodium 3-dodecylaminopropane sulfonate, N-alkyltaurines and betaines.

The disinfecting composition comprising nanosilver obtained by the method of the present invention may be stabilized in the biomatrix and may be applied directly, or after further processing as disclosed hereinabove, in the environment to be treated, cleaned or depolluted. For instance the nanosilver particles may be dispersed at, or in the surrounding of, the location where bacteria have to be removed by any suitable means or application methods. The nanosilver component of the composition is able to interact with the bacteria's cell components, thus effectively destroying them and reducing the total bacterial cell number to an admissible level.

The use of a nanosilver-containing liquid composition such as described above may be for cleaning, decontaminating, disinfecting or sterilizing a solid surface or a volume of a gas or liquid. When said liquid composition according to the present invention is used as a disinfecting or sterilizing composition (e.g. by dispersion into a liquid or gas), it is typically applied in appropriate conditions, including concentrations and application time, which the skilled person can readily determine from the standard knowledge in the art of disinfection and sterilization.

When the disinfecting liquid nanosilver-containing composition of the invention is applied onto a solid surface, it is preferred for safety regulations to employ a ready-to-use diluted formulation obtained by mixing a suitable amount of a concentrated composition with water, and then moisturizing the said solid surface with the diluted formulation obtained during such time until complete wetting of the solid surface is achieved (which, as is known from the skilled person, may depend upon the surface porosity).

As will be understood to those skilled in the art, the preferred amount of the disinfecting liquid nanosilver-containing composition to be used will widely vary with the type and amount of micro-organisms present on the solid surface or present in the liquid or gas to be treated.

With respect to the above use of liquid nanosilver-containing compositions according to this invention as a disinfectant, the following application methods are more particularly recommended:

immersion of the product to be treated into the said nanosilver-containing composition, spraying of the disinfecting composition onto a solid surface to be treated, and incorporation of the disinfecting (diluted or concentrated) composition into water to be treated (particularly swimming pool water, industrial process water, waste water and the like).

Therefore, the disinfecting liquid nanosilver-containing compositions according to the present invention are especially useful for:

(a) the disinfection and hygiene of hospital and laboratory premises, industrial premises (such as milk dairies, cheese dairies, malt houses, breweries, facilities for the production of mineral water, wine, spirits, fruit and vegetable juices; greenhouses; cowsheds, hen houses and stables; packaging lines for foodstuffs, drinks or pharmaceuticals; interiors of aeroplanes and boats) and the contents of said premises, especially the equipment or instruments within said premises;

(b) the sterilization of aseptic enclosures such as incubators for premature animals or growing axenic animals;

(c) the treatment of *legionella* in air-conditioning systems;

(d) the disinfection and hygiene of storage containers (especially silos) and pipelines for conveying liquid or solid products such as foodstuffs (sugar, tea, coffee, cereals, drinks) and animal feed;

(e) the disinfection and hygiene of swimming pools and other balneotherapy equipments (in which case the composition will preferably be surfactant-free);

(f) the disinfection of systems for the production, transport and storage of drinking water (for instance in wells or storage containers), in which case the composition will preferably be surfactant-free; and (g) the protection of outdoor crops (such as cereals, tomatoes, banana plantations, hydroponic cultures including witloof, seeds, tubercules and the like), by virtue of its bactericidal, fungicidal, antiviral and antiparasitic properties.

The high and selective anti-microbial activity of the nanosilver composition obtained by the method of the present invention has a broad range of domestic as well as industrial applications such as, but not limited to, water disinfection, treatment of algae growth in water, cleaning product, and the formulation of antimicrobial coatings, e.g. for use in medical applications or in the processing of nutrition or other materials for human or animal consumption (especially due to the absence or minimal effect on eukariotic cells or organisms), for use in the antimicrobial protection of textile products, for use in topical medical preparations for preventing infectious or microbial contaminations of exposed tissues such as, but not limited to, creams, ointments or lotions, or for use as catalysts in chemical or other transformation processes. Each of the aforesaid uses may be achieved by means of nanosilver in suspension as well as by incorporating nanosilver in polymers and/or other types of coatings.

A third aspect of the present invention relates to the production of metallic nanoprecipitates by probiotic and other bacteria that can surprisingly be used as an algicide agent (e.g. against *Chlorella vulgaris*, but not limited thereto) in drinking water, aquarium or pond or swimming pool water, or in other reservoirs with fresh water or salt water, in polymers and paints, in surface coatings and other materials to protect against soft fouling (aesthetic aspect) or hard fouling (materials deterioration). A fourth aspect of the present invention relates to the production of metallic nanoprecipitates by probiotic and other bacteria that can surprisingly have a herbicidal effect against certain dicotyledonous or monocotyledonous plants or an effect against different types of lower plants, like moss, both in diluted form in water or when further processed by mechanical, enzymatic and/or physico-chemical means. The choice of the relevant plant for this purpose is not a critical parameter of the present invention. Suitable plants for this purpose include, among others, dicotyledonous plants such as tobacco (*Nicotiana tabacum*), duck weed (*Lamna* sp.), soybean (Glycine max), apple, sugarbeet, *Arabidopsis thaliana*, alfalfa, petunia, cotton, carrot, celery, cabbage, cucumber, pepper, canola, tomato, potato, lentil, flax, broccoli, bean, lettuce, oilseed rape, cauliflower, spinach, brussel sprout, artichoke, pea, okra, squash, kale, collard greens, tea, coffee and *Selaginella lepidophylla*. They also include monocotyledonous plants such as rice *Oryza sativa*, corn, barley, maize, sunflower (*Helianthus annuus*), wheat, oats, millet, sorghum, amaranth, onion, asparagus and sugar cane.

The above aspects of the present invention are especially useful in the following fields:

inhibition of algal growth in aquarium water, in drinking water distribution systems for animals and humans, in water distribution systems for horticulture, in ponds, in swimming pools, in filtration systems to treat water from ponds or swimming pools, and in different types of sprinkling systems;

inhibition of algal growth on surfaces, including surfaces in contact with water such as ship hulls;

use in paints, polymers or coatings for the treatment of surfaces against algae, and including algae growth on surfaces of higher organisms like plants;

inhibition of growth of moss or other unwanted plants, both monocotyls or dicotyls, by exposure of leaf, stem, flower or root systems to colloidal silver, e.g. colloidal silver produced by probiotic bacteria and precipitated thereon according to the above-mentioned production method; and inhibition of growth of certain plants or weeds on surfaces by coating or otherwise exposing these surfaces to colloidal silver, e.g. colloidal silver produced by bacteria and precipitated thereon according to the above-mentioned production method.

The following examples are provided as an illustration, without any limiting intention, of certain embodiments of the method and disinfecting compositions according to the present invention.

EXAMPLE 1

Preparation of Nanosilver

A culture of *Lactobacillus fermentum* Beijerinck 1901 AL (ATCC 11976, LMG 8900, from intestine of an 8-days old breast fed infant) was propagated in MRS broth (commercially available from Oxoid, Basingstoke, United Kingdom) under micro-aerophilic conditions at 37° C. for 15 hours.

Cells were harvested from MRS by centrifugation at 3,000 g for 10 minutes at 15° C. and washed 2 times with milliQ water, then re-suspended in milliQ water to a final optical density of 1.5 at 600 nm ($OD_{600}$). Sodium hydroxide was added to the cell suspension from a 1 N NaOH stock solution such as to reach final concentrations of 0.05 N NaOH and 0.10 N NaOH, respectively.

An Ag (I) stock solution of 425 mg $AgNO_3$ and 225 mg $NH_4Cl$ in 50 mL milliQ water was prepared. One volume of this Ag(I) stock solution was added to ten volumes of the cell suspensions with 0.05 and 0.10 N NaOH, respectively. These mixtures were allowed to incubate under visible light at 25° C., under mild stirring conditions (100 rotations per minute on shaker) for 30 minutes. A final solution of 5.0 mM Ag(0) (535 mg Ag(0)/L) deposited on Lactobacillus fermentum biomass was obtained, herein referred as "nanosilver" or "nano-Ag". The coated Lactobacillus fermentum cells were centrifuged and washed three times with milliQ water in order to remove growth medium residues and other additives, by repeatedly centrifuging, decanting and re-suspending the composition in fresh milliQ water. The final nano-Ag concentration was consequently adjusted. The composition was then either diluted with milliQ water or concentrated by centrifugation at 3,000 g and re-suspended in milliQ water according to the needs of the end user.

EXAMPLE 2

XRD Analysis of Nanosilver

X-ray diffraction (XRD) analysis of the biomass with silver particles obtained in example 1 and further dried at 30° C. was performed with a Siemens Diffractometer D5000 with Bragg-Brentano optics (commercially available from Siemens, Munich, Germany). X-rays were generated by a copper X-ray tube with power 1.6 kW (40 kV, 40 mA). Measurements were made between 25 and 90 degrees 2-theta with a tep time of 1.6 s and a step size of 0.02 degree. The resulting spectrum (not shown) indicates the presence of the X-ray diffraction pattern of silver metal and sodium oxide. The latter is a residue of the sodium hydroxide used in the preparation of the nanosilver.

EXAMPLE 3

EDX Analysis of Nanosilver

Energy Dispersive X-ray (EDX) analysis of dried biomass with nanosilver as obtained in example 1 and further dried at 30° C. was performed with a JSM6100 Scanning Electron Microscope with EDX detector (available from JEOL USA, Inc.) with a resolution corresponding to an incident energy of 20.0 keV. Analysis results are listed in Table 1 (both as weight % and atomic %) and clearly demonstrate the presence mainly of organic matter (due to the high content of carbon and oxygen) and silver, the combination of which amounts to about 91 weight % of the dry matter. The rest of the dried product consisted of trace elements Ca, Mg, Si, P, S and Cl mostly due to mineral residues from the dried biological matrix.

TABLE 1

| element | Weight % | Atomic % |
|---|---|---|
| C | 55.90 ± 0.28 | 69.18 ± 0.16 |
| O | 26.21 ± 0.08 | 24.35 ± 0.15 |
| Na | 4.97 ± 0.02 | 3.21 ± 0.00 |
| Mg | 0.85 ± 0.06 | 0.52 ± 0.04 |
| Si | 0.19 ± 0.06 | 0.10 ± 0.03 |
| P | 1.64 ± 0.04 | 0.79 ± 0.02 |
| S | 0.22 ± 0.01 | 0.11 ± 0.01 |
| Cl | 0.31 ± 0.03 | 0.13 ± 0.014 |
| Ag | 8.51 ± 0.20 | 1.17 ± 0.03 |
| Ca | 1.22 ± 0.18 | 0.45 ± 0.07 |

EXAMPLE 4

Antimicrobial Activity of Nanosilver on A Solid Growth Medium for Escherichia coli 100 mL of a silver suspension with an Ag concentration of 5 mM, in the form of nanosilver deposited on Lactobacillus fermentum biomass as obtained in example 1, was plated onto a solidified growth medium for culturing Escherichia coli (Luria Bertani Agar). As a control, 100 mL of a solution of 5 mM $AgNO_3$ in sterile milliQ water with 0.1 N NaOH were plated on the same growth medium. This setting agreed with a total amount of 0.05 mg Ag per agar plate, or 11 mg Ag per $m^2$ of total surface area. This experiment was repeated with twofold the latter concentrations, i.e. with 0.11 mg Ag per agar plate or 22 mg Ag per $m^2$ of total surface area.

By plating these silver suspensions, a homogeneous layer of $Ag(I)NO_3$, or nano-Ag respectively, was applied onto the solidified growth media.

Figure 1:
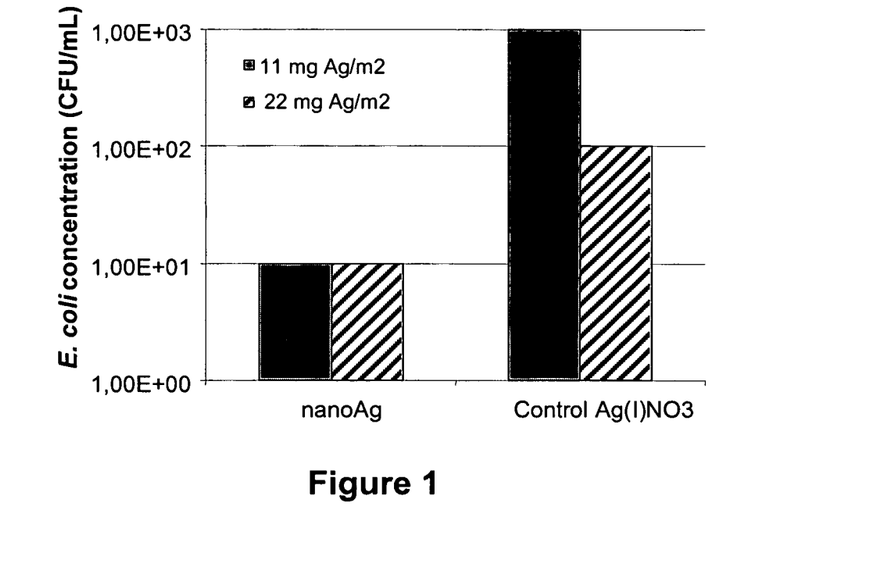
FIG. 1 shows the antimicrobial effect of treatment with nanosilver particles according to an embodiment of the invention at different concentrations on the total cell count and survival of *E. coli*.
Figure 2:
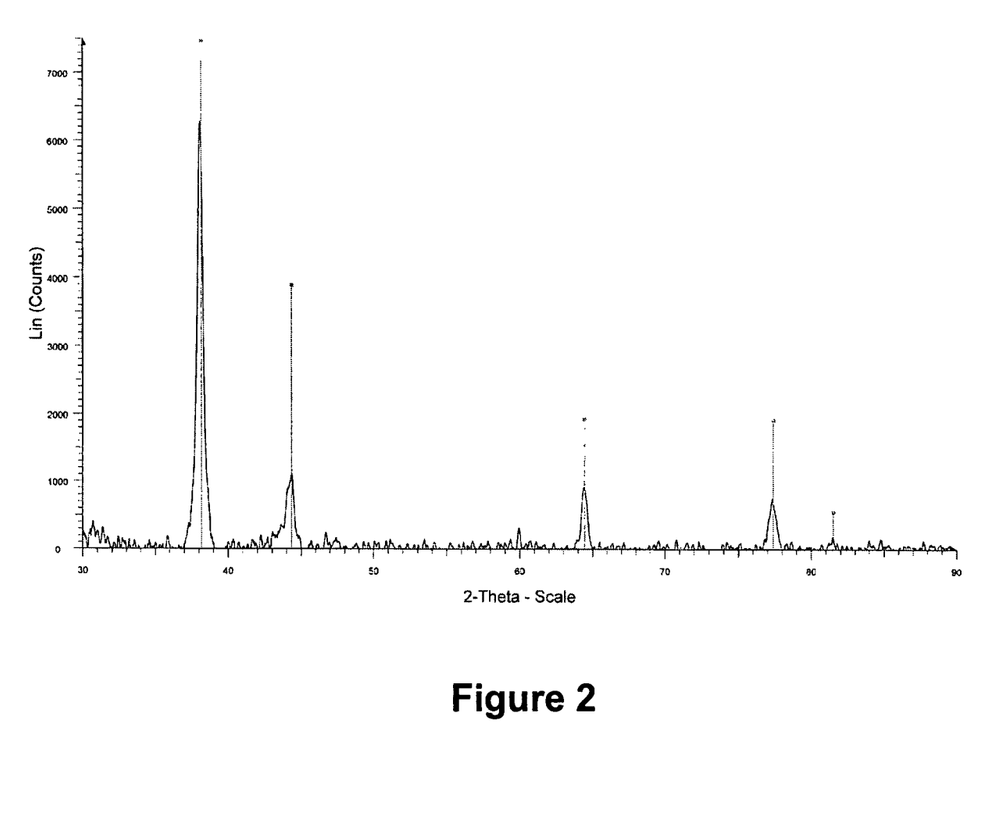
FIG. 2 shows the X-Ray diffraction analysis spectrum of nanosilver particles according to an embodiment of the invention.

After pre-treating the solidified growth medium in this way, 100 µL of a $2\times10^6$ CFU/mL Escherichia coli suspension in physiological solution (8.5 g NaCl/L in sterile water) was plated on the pre-treated agar plates. The plates were then incubated during 24 hours at 30° C. and colonies were counted. The count results are illustrated by FIG. 1. At nano-Ag concentrations of 11 mg Ag/$m^2$ and 22 mg Ag/$m^2$, no viable cells of E. coli could be detected on the treated solid growth medium (<detection limit (D.L.)=$1\times10^1$ CFU/ml). Thus nano-Ag treatment at these concentrations resulted in E. coli cell reduction from $2\times10^6$ CFU/ml to less than $1\times10^1$ CFU/ml (D.L.). At $Ag(I)NO_3$ concentrations of 11 mg Ag $m^2$ and 22 mg Ag/$m^2$ there was a significant E. coli cell reduction from $2\times10^6$ CFU/ml to $4\times10^2$ CFU/ml and $1\times10^2$ CFU/ml, respectively.

As a control, E. coli suspensions with a concentration of $2\times10^6$ CFU/mL were plated onto untreated growth medium, i.e. without Ag, and onto the same growth medium treated with 100 µL of sterile mQ water with only Lactobacillus fermentum ATCC 11976, at the same concentration as the nano-Ag treatment, but without nano-Ag. No inhibitory effect was observed on the total count of these bacteria. Consequently, the inhibitory effect observed for nanoAg and Ag(I) can be attributed to Ag treatment, and not to either the treatment procedure or the Lactobacillus strains used in this experiment.

EXAMPLE 5

Antimicrobial Activity in Suspension for Different Pathogenic Bacteria

The survival of pathogenic Escherichia coli, Salmonella typhimurium, Staphylococcus aureus and Listeria monocytogenes cultures diluted in physiological solution containing different concentrations (0 mg/L, 0.10 mg/L, 1.0 mg/L, 10 mg/L and 50 mg/L) of the nano-Ag composition obtained in example 1, was tested. Nano-Ag was applied in a physiological solution containing a living culture of one of the above-mentioned pathogenic bacteria. Physiological solution included 8.5 g NaCl per 1 L water and was prepared to have an osmotic potential neutral towards bacterial cells, thus not killing them due to osmotic stress. Control treatments consisted of a bacterial culture in physiological solution in the absence of nano-Ag.

A stock solution of 100 mg nanoAg/L in mQ water was prepared and added to bacterial cultures diluted in physiological solution in amounts suitable for achieving the final nano-Ag concentrations shown in table 2.

Treatment was repeated independently for each pathogenic bacterial species mentioned above, with "bacterial culture" representing a diluted liquid broth with the bacterial species in exponential growth phase, diluted in physiological solution to a final cell concentration of $10^4$-$10^5$ CFU/ml. Each treatment was done in duplicate. All incubations were effected in sterile, capped test tubes which were incubated under shaking at 37° C. during 72 hours. After incubation, 100 µL of each test tube was plated onto a Trypticase Soy Agar (TSA) solid growth medium and colonies were counted. Results of these counts are shown in Table 2 for the different pathogens tested.

TABLE 2

| nano-Ag concentration | Pathogen (CFU/mL) | | | |
|---|---|---|---|---|
| (mg Ag/L) | E. coli | S. aureus | Salmonella | Listeria |
| 0 | $1.1 \times 10^2$ | $1.3 \times 10^2$ | $1.0 \times 10^3$ | $1.5 \times 10^1$ |
| 0.10 | $4.6 \times 10^1$ | 1 | 5 | $1.0 \times 10^1$ |
| 1.0 | 0 | 0 | 0 | 2 |
| 10 | 2 | 0 | 0 | 0 |
| 50 | 0 | 0 | 0 | 0 |

Table 2 shows that a concentration of 1 mg/L nanoAg as obtained in example 1 was sufficient to reduce the number of viable cells of *E. coli*, *S. aureus* and *S. typhimurium* within 72 hours to a cell concentration <10 CFU/mL (i.e. below the detection limit). Significant cell death was already observed at a concentration of 0.10 mg/L. With respect to *Listeria*, a decrease of the concentration of viable cells below the detection limit was obtained at 10 mg/L nanoAg. We thus conclude that nanoAg as obtained in example 1, at concentrations of 1.0 mg/L or lower in liquid cell suspensions, act as a strong antimicrobial agent that significantly and effectively eliminates viable pathogenic bacteria from the liquid.

EXAMPLE 6

Antimicrobial Activity of Nano-Ag in Suspension in Combination with *Artemia franciscana*

Sterile artificial seawater (Instant Ocean$^R$, available from Aquarium Systems USA) was prepared in milliQ water by autoclavation. All treatments were set up in 20 mL aliquots of sterile artificial seawater in 50 mL Falcon tubes. Each treatment (performed in triplicate) consisted of 20 axenic *Artemia nauplii* in 20 mL artificial seawater, supplemented with a combination of $10^5$ CFU/mL (colony forming units) *Vibrio campbellii* LMG21363 and/or nano-Ag as obtained in example 1 at a final concentration as shown in table 3. The pathogenic bacterium V. campbellii was thus incubated together with its host organism *Artemia franciscana*.

The following tests were set up:
*Artemia franciscana*+$10^5$ CFU/ml *Vibrio campbellii*
*Artemia franciscana*+$10^5$ CFU/ml *Vibrio campbellii*+100 mg nanoAg/L
*Artemia franciscana*+$10^5$ CFU/ml *Vibrio campbellii*+10 mg nanoAg/L
*Artemia franciscana*+$10^5$ CFU/ml *Vibrio campbellii*+1.0 mg nanoAg/L
*Artemia franciscana*+$10^5$ CFU/ml *Vibrio campbellii*+0.1 mg nanoAg/L
*Artemia franciscana*+0.10 mg nanoAg/L
*Artemia franciscana*+100 mg nanoAg/L
*Artemia franciscana*+10 mg nanoAg/L
*Artemia franciscana*+1.0 mg nanoAg/L, and
*Artemia franciscana*+0.10 mg nanoAg/L After 48 hours incubation, the concentration of *V. campbelli* in the sterile artificial seawater with *Artemia franciscana* was determined by plate counting on a specific *Vibrio* growth medium. The average treatment results are shown in Table 3 below (wherein D.L. refers to the detection limit).

TABLE 3

| Concentration nanoAg (mg Ag/L) | Survival of *Vibrio campbellii* pathogenic bacteria |
|---|---|
| 0 | $1.0 \times 10^5$ CFU/mL |
| 0.10 | $3.0 \times 10^2$ CFU/mL |
| 1.0 | <$10^1$ CFU/ml (D.L.) |
| 10 | <$10^1$ CFU/ml (D.L.) |
| 100 | <$10^1$ CFU/ml (D.L.) |

It was furthermore noted that at concentrations of 0.10 and 1.0 mg/L of nanoAg, there was no significant effect on the survival rate (80%) of *Artemia franciscana* compared to untreated controls. This indicates that nano-Ag produced according to example 1 has no toxic or inhibitory effect on higher organisms at these concentrations.

EXAMPLE 7

Determination of Effective Contact Time for Antimicrobial Activity

The goal of this test was to determine a suitable contact time of the nanoAg composition of example 1 with pathogenic bacterial cultures *Escherichia coli*, *Salmonella typhimurium*, *Staphylococcus aureus* or *Listeria monocytogenes* diluted in physiological solution, in order to obtain effective antimicrobial activity at concentrations of 0.1 and 1 mg/L Ag, respectively.

These nanoAg concentrations were applied to bacterial cultures in a physiological solution (8.5 g NaCl in 1 L water) prepared to have an osmotic potential that is neutral towards bacterial cells, thus not killing them due to osmotic stress.

Control treatment consisted of a bacterial culture in physiological solution without the nano-Ag composition.

A stock solution of 100 mg nanoAg/L in mQ water was prepared and added to bacterial cultures (in the same meaning as in example 5) in physiological solution in suitable amounts for providing the desired final nano-Ag concentrations.

Incubations (performed in duplicate) were effected in sterile, capped test tubes by shaking at 37° C., and cell counts were then determined at different contact times (sampling events). At each sampling event, 100 µL of each treatment was plated onto a Trypticase Soy Agar (TSA) solid growth medium and colonies were counted. Results obtained after 15 hours, 16 hours, 17 hours, 18 hours and 40 hours respectively are shown in Table 4 below (wherein ND means non-detectable, i.e. below the detection limit).

TABLE 4

| Contact time (hours) | Conc. (ppm) | Pathogen | | | |
|---|---|---|---|---|---|
| | | Salmonella | Staphylococcus | E. coli | Listeria |
| 15 | 0 | 1.0E+05 | 2.2E+02 | 4.5E+03 | 4.9E+03 |
|  |  | 1.0E+04 | 1.1E+02 | 6.1E+03 | 4.2E+03 |
|  | 1 | ND | ND | ND | 1.0E+01 |
|  |  | ND | ND | ND | 2.0E+01 |
|  | 0.1 | ND | 5.0E+01 | ND | 3.4E+03 |
|  |  | ND | 1.0E+02 | 1.0E+01 | 3.9E+03 |
| 16 | 0 | 2.0E+04 | 1.6E+02 | 2.7E+03 | 5.6E+03 |
|  |  | 7.3E+03 | 1.3E+02 | 4.0E+03 | 5.1E+03 |
|  | 1 | ND | ND | ND | ND |
|  | 0.1 | ND | 6.0E+01 | ND | 2.0E+03 |
|  |  | ND | 4.0E+01 | ND | 2.1E+03 |
| 17 | 0 | 1.2E+04 | 1.5E+02 | 3.1E+03 | 5.6E+03 |
|  |  | 1.0E+04 | 1.7E+02 | 3.2E+03 | 4.7E+03 |
|  | 1 | ND | ND | ND | ND |
|  | 0.1 | ND | 1.0E+01 | ND | 1.1E+03 |
|  |  | ND | 5.0E+01 | ND | 8.8E+02 |
| 18 | 0 | 1.0E+04 | 1.6E+02 | 2.2E+03 | 3.5E+03 |
|  |  | 1.0E+04 | 7.0E+01 | 2.3E+03 | 2.4E+03 |
|  | 1 | ND | ND | ND | ND |
|  | 0.1 | ND | 1.0E+01 | ND | 9.2E+02 |
|  |  | ND | ND | ND | 2.2E+03 |
| 40 | 0 | 1.0E+04 | 1.0E+01 | 1.5E+03 | 9.0E+01 |
|  |  | 1.9E+04 | 1.0E+01 | 1.9E+03 | 7.0E+01 |
|  | 1 | ND | ND | ND | ND |
|  | 0.1 | ND | ND | ND | ND |

EXAMPLE 8

Preparation of Nanosilver Compositions at Different Weight Ratios of Silver to Biomass Cell Dry Weight A stock solution of silver (I) was prepared in liquid ammonia (28% by volume NH3 in water) in a final concentration of 425 g $AgNO_3$/L (=50 mM $AgNO_3$). A culture of *Lactobacillus fermentum* was then prepared as in example 1.

2.8 g (wet weight) of the centrifuged cell pellet was resuspended in 3 different amounts (50 ml, 100 ml and 1L) milliQ water in order to obtain reaction mixtures referred as A, B and C, respectively.

NaOH was then added to each test tube from a 1 N NaOH stock solution in milliQ water, to obtain a normality of 0.10 N NaOH in the above mentioned suspension.

Consequently, the silver (I) stock solution was added as follows:

Reaction mixture A: 0.24 mL of silver(I) stock solution was added to obtain a final concentration of 1.30 g Ag/L (or 12 mM) Ag. An almost immediate precipitation reaction (brown-reddish precipitate) on the 56 g/L biomass (-wet weight) took place. Assuming an average dry weight ratio of the centrifuged biomass between 10 and 30%, a silver to cell dry weight ratio between 1:4 and 1:12 was obtained.

Reaction mixture B: 2.4 mL of silver(I) stock solution was added to obtain a final concentration of 5.78 g Ag/L (55 mM) Ag. An almost immediate precipitation reaction (brown-reddish precipitate) on the 28 g/L biomass(-wet weight) took place. Since the dry weight of centrifuged biomass is on average 10-30%, a silver to cell dry weight ratio between 2:1 and 0.7:1 was obtained. The pH during this reaction was 11.6.

Reaction mixture C: 24 mL of silver(I) stock solution was added to obtain a final concentration of 5.78 g Ag/L (55 mM) Ag. An almost immediate precipitation reaction on the 2.8 g/L biomass(-wet weight) took place. Since the dry weight of centrifuged biomass is on average between 10-30%, a silver to cell dry weight ratio between 20:1 and 7:1 was obtained.

The reaction mixtures were allowed to rest during 30 minutes, after which the nano-Ag composition formed was harvested.

The resulting nano-Ag precipitate was centrifuged down together with the biomass at 3,000 g for 10 minutes at 15° C., and then washed two times with milliQ water in order to remove any residual ammonia and other water soluble components from the production process. The nano-Ag purified pellet product was then analyzed (example 9), or further diluted in milliQ water to appropriate concentrations of nanoAg for further testing.

EXAMPLE 9

XRD Analysis of Nanoag Produced at a Silver to Biomass Cell Dry Weight Ratio of 0.7:1

XRD analysis of a biomass with nanosilver particles produced with a silver to biomass cell dry weight ratio of 0.7:1 according to example 8, then dried in an oven at 100° C. during 24 hours, was performed as explained in example 2. Only the X-ray diffraction pattern of silver metal could be detected in this XRD spectrum. Since it can safely be estimated that crystalline trace elements below 5% by weight in the dried product cannot be detected by XRD, it can be roughly estimated that at least 95% of silver detected by this XRD analysis was in the Ag(0) state.

EXAMPLE 10

Post-Treatment of Nanosilver with $H_2O_2$

Washed nano-Ag pellets obtained according to example 1 or example 8, were post-treated with 30% (by volume) $H_2O_2$ in water. To this effect, the pellets were suspended in $H_2O_2$ at concentrations of up to 6 g Ag/L $H_2O_2$ (30%). More stable precipitates were obtained. A suspension of the obtained precipitates was then further diluted in milliQ water to obtain appropriate concentrations of nanoAg for further testing.

EXAMPLE 11

Anti-Microbial Properties of Nanoag Without or After $H_2O_2$ post-treatment

NanoAg formulations were prepared as described in example 8 at different silver to biomass cell dry weight ratios of 7:1, 1:10 and 0.7:1 respectively (samples herein referred as A, B and C, respectively). Additionally, the nanoAg preparations obtained at a silver to biomass cell dry weight ratio 0.7:1 was further treated with $H_2O_2$ as described in example 10, thereby yielding a fourth sample referred as D.

Figure 3:
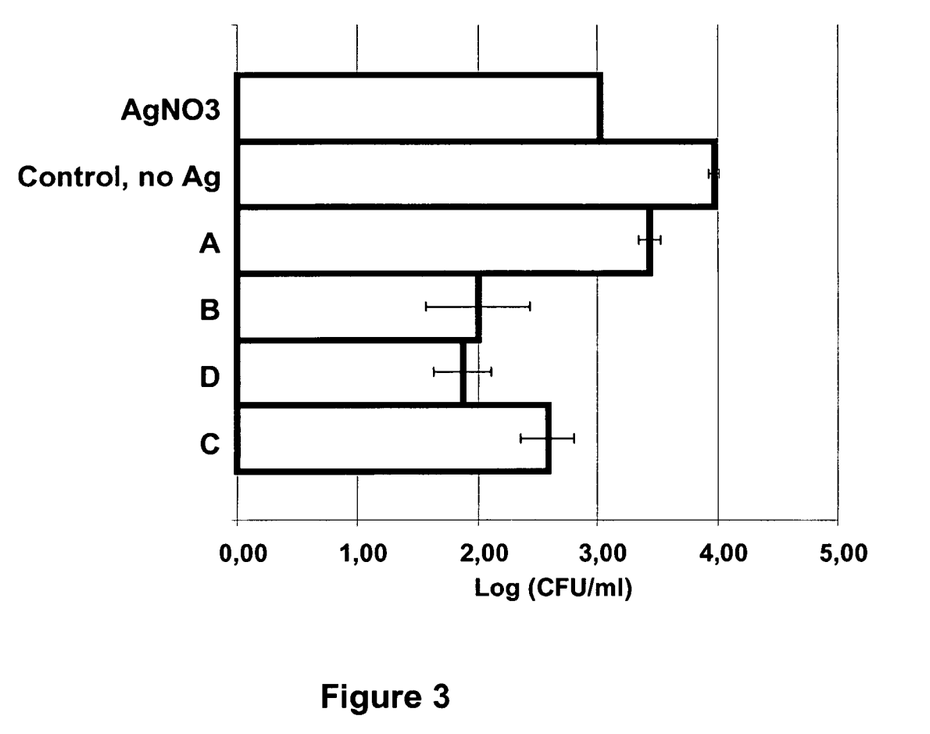
FIG. 3 shows the effect of the silver to cell dry weight ratio during production of nanosilver particles according to an embodiment of the invention onto the antimicrobial activity of said particles against *Salmonella typhimurium*.

In order to assess the effect of the silver to biomass cell dry weight ratio onto anti-microbial activity of the nanoAg products, a cell suspension of $1 \times 10^4$ CFU/mL of *Salmonella typhimurium* was made in sterile physiological solution and dispensed over different test tubes. Samples A, B, C and D were added to these test tubes until a final concentration of 0.05 mg/L (or 50 ppb) of nanoAg in each test tube was obtained. As controls, bacterial cultures were incubated with $AgNO_3$ at 0.05 ppm and without any silver. The test-tubes were capped and incubated while shaking at 37° C. in duplicate. After 4.5 hours incubation, samples were taken, dilution series in physiological solution were made, and plating on TSA medium was followed by incubating plates at 37° C. overnight in order to allow for the determination of total *Salmonella* count. The results of these counts are shown in FIG. 3 in the form of an average cell count and standard deviation of two independent replicates. A substantial reduction of the bacteria count has been observed after 4.5 hours incubation in the presence of 0.05 ppm nanoAg obtained by the method of example 8. FIG. 3 shows that the higher the silver to cell dry weight ratio, the less reactive the resulting nanoAg was towards antimicrobial activity. Also, treatment of the nanoAg product with $H_2O_2$ significantly increased its anti-microbial activity.

EXAMPLE 12

Determination of Particle Size of Nanosilver by Means of Transmission Electron Microscopy In order to prepare thin sections for analysis by TEM, pellets of bacteria were fixed in 0.1 M of a cacaodylate buffer (pH 7.4) containing 2.5% glutaraldehyde and 2% formaldehyde, and embedded in 3% low melting agarose (from Difco Laboratories, Detroit, Mich., USA). These samples were post-fixed in 1% osmium tetroxide. Between and after fixation steps, samples were washed with distilled water. Afterwards, samples were dehydrated in increasing concentrations of ethanol and, finally, in anhydrous propylene oxide. After embedding in Epon-Spurr medium, the specimen blocks were trimmed with a TM60 trimming unit (from Reichert-Jung A. G., Vienna, Austria) to obtain a cutting face of 0.5×1 mm2-1×2 mm2, and ultra-thin sections in the gold to mat silver interference color range were cut using the Ultracut microtome (from Reichert-Jung A.G., Vienna, Austria). The sections were brought on pioloform and carbon coated copper grids (200 mesh). Once this was done, thin sections were stained with 2% uranyl acetate and then with lead citrate to determine the ultra-structure of the cells. Chemicals and grids were obtained from Agar Scientific (Stansted, United Kingdom). Imaging was performed with a EM208S transmission electron microscope (from FEI, Eindhoven, the Netherlands) operating at 80 kV.

TEM images (not shown) have been obtained for the nanosilver particles resulting from reaction mixtures A, B and C described in example 8. These images confirm that spherical nanosilver particles were obtained in the composition in the form of precipitates on the bacterial cell-surface and in suspension between the biomass.

Particle sizes for nanoAg resulting from reaction mixture A (ratio 1:10): for the 35 nanoparticles measured, the diameter ranged from 3.3 nm to 72 nm with an average of 14 nm, the particle surface area ranged from 6.4 to 2,996 $nm^2$, and therefore sfericity ranged from 0.14 to 0.97;

Particle sizes for nanoAg resulting from reaction mixture B (ratio 1:1): for the 202 nanoparticles measured, the diameter ranged from 3 nm to 116 nm with an average of 15 nm, the particle surface area ranged from 6 to 4,805 $nm^2$, and therefore sfericity ranged from 0.12 to 0.96;

Particle sizes for nanoAg resulting from reaction mixture C (ratio 10:1): for the 56 nanoparticles measured, the diameter ranged from 3.3 nm to 56 nm with an average of 16 nm, the particle surface area ranged from 6.4 to 1,841 $nm^2$, and therefore sfericity ranged from 0.15 to 0.95.

EXAMPLE 13

Preparation of Colloidal Nano-Gold

A stock solution of gold(III) was prepared in milliQ water, in a final concentration of 7.5 g $AuCl_3$/L. A culture of *Lactobacillus fermentum* was obtained according to example 1.

A centrifuged cell pellet with a wet weight of 2.5 g was added to 100 mL of milliQ water.

NaOH was added from a 1 N NaOH stock solution in milliQ water, to obtain a normality of 0.10 N NaOH in the above mentioned suspension.

To this suspension, consequently, 10 mL of gold(III) stock solution was added to obtain a final concentration of 75 mg Au(III)/100 mL in the form of AuCl3-Au (3.8 mM Au). Au(0) precipitation onto the 2.5 g/100 mL biomass(-wet weight) was completed within 4 hours. Since the dry weight of centrifuged biomass is on average between 10-30%, a gold to cell dry weight ratio between 1:3 and 1:10 was obtained.

The reaction was allowed to continue during 4 hours, after which the nanogold particles were harvested. This purple precipitate was centrifuged down at 3,000 g for 10 minutes at 15° C. and washed 2 times with milliQ water to remove water soluble components from the production process.

EXAMPLE 14

XRD Analysis of Nano-Gold

Figure 4:
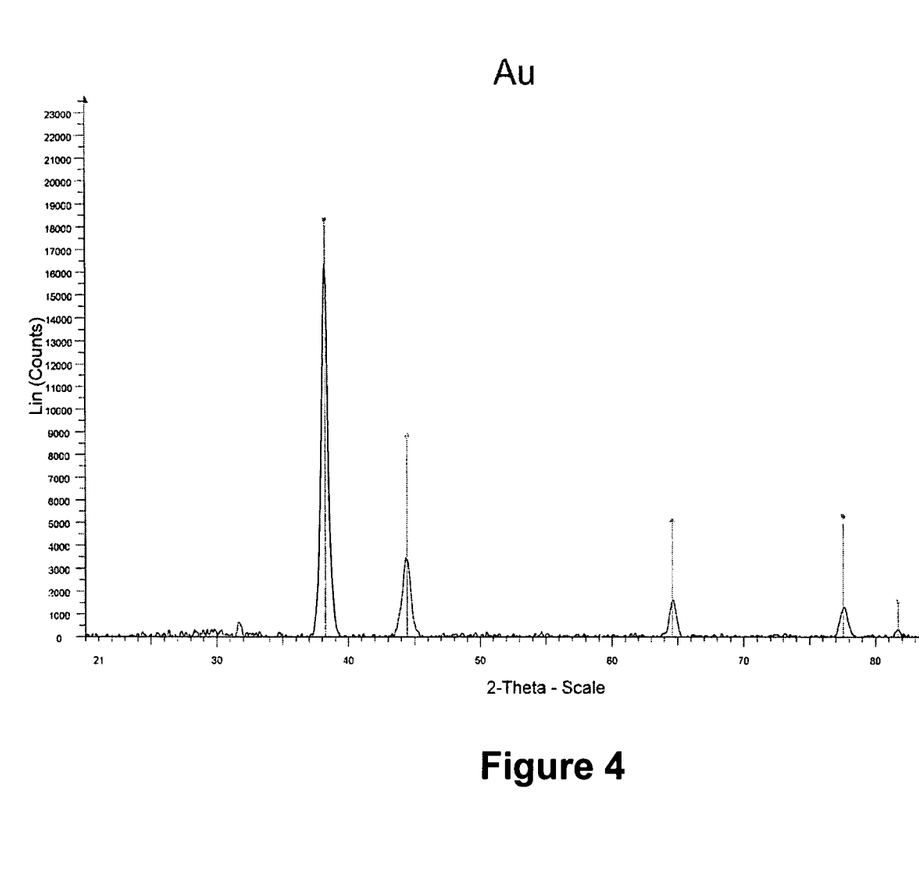
FIG. 4 shows the X-Ray diffraction analysis spectrum of nanosilver particles according to another embodiment of the invention.

XRD analysis of the biomass with gold particles from example 13, dried in an oven at 100° C. during 24 hours, was performed with a Siemens Diffractometer D5000 with Bragg-Brentano optics as explained in example 2. The resulting spectrum is shown in FIG. 4 and indicates the presence of X-ray diffraction peaks of $Au^0$ only.

EXAMPLE 15

Bioprecipitation Efficiency and Recovery on Biomass at Different Silver to Biomass Cell Dry Weight Ratios In order to assess biomass influence on the bioreduction of Ag(I) to Ag(0) nanoparticles, the recovery on biomass and in solution after bioreduction at different Ag:CDW ratios was determined.

Nanosilver formulations at different Ag:CDW ratios were prepared as described in example 8. Silver recovery percentages were determined after 4 hours of biomass incubation with Ag(I) and after fractionation between soluble phase (in solution) and precipitate phase (on biomass) by centrifugation at 7,000 g during 10 minutes. Results of this investigation are shown in Table 8 below.

TABLE 8

| Sample (Ag:CDW ratio) | mg Ag/L in solution | mg Ag/L on biomass | Total recovery |
|---|---|---|---|
| A (1:10) | 76 | 1,295 | 100% |
| B (1:1) | 819 | 5,308 | 100% |
| C: Ag:CDW = 10:1 | 1,612 | 4,844 | 100% |

From these results, it is clear that silver recovery as biomass-associated particles was higher when Ag:CDW ratios were lower. For instance a Ag:CDW ratio of 1:10 provides an acceptable Ag0 recovery (about 95%) from Ag(I) in solution by means of bioreduction.

EXAMPLE 16

Algicidal Properties of A Nanosilver Formulation without Hydrogen Peroxide Post-Treatment A nanosilver formulation was prepared as described in example 8 at a silver to biomass cell dry weight ratio of 1:4.

In order to assess the algicidal effect of this formulation, test tubes containing 10 mL BG11 medium (as described by Stanier et al. in Bacteriol. Rev. (1971) 35:171-205, were inoculated with 0.5 mL of an actively growing liquid BG11 culture of *Chlorella vulgaris* and incubated at 20° C., 65% relative humidity and 1000 Lux (16 hours/day). Growth was evaluated after 2 weeks by spectrophotometric measurement. Different concentrations of the nanosilver formulation, ranging from 20 mg Ag/L to 0.01 mg Ag/L, were tested by dosage in the test tubes. The MIC value is the lowest test concentration at which complete inhibition of organism growth was observed. The MIC value of this nanosilver formulation against *Chlorella vulgaris* was determined to be 0.125 mg Ag/L.

The invention claimed is:

1. A method for producing a composition comprising colloidal atomic nanosilver comprising incubating probiotic bacteria that is a *Lactobacillus* species with an aqueous solution comprising at least about 4 mM of a silver salt;
   wherein the incubation time is from about 1 second to about 30 minutes; and
   wherein the incubation is performed at a pH within a range of from about 8 to about 12.

2. The method according to claim 1, wherein said aqueous solution comprises at least about 4 mM of a silver salt and further comprises ammonia, an ammonium salt, or a mixture thereof; and an alkali metal hydroxide.

3. The method according to claim 2, wherein the amount of ammonia, ammonium salt, or mixture thereof is sufficient to form $Ag(NH_3)^+$ or $\{Ag(NH_3)_2\}^+$ complex.

4. The method according to claim 2, wherein said alkali metal hydroxide is sodium hydroxide or potassium hydroxide.

5. The method according to claim 1, wherein the ratio of silver weight to cell dry weight of the bacteria is within a range from about 0.05 to about 20.

6. The method according to claim 1, wherein said salt is silver nitrate or silver chloride.

7. The method according to claim 1, further comprising removing at least part of said probiotic bacteria from the incubation mixture by means of mechanical, enzymatic, or physicochemical treatment.

8. The method according to claim 1, further comprising:
   centrifuging the incubation mixture into a solid portion comprising the composition having colloidal atomic nanosilver and a liquid portion, and
   separating said solid portion from the liquid portion.

9. The method according to claim 1, further comprising the step of treating said composition comprising colloidal atomic nanosilver with a peroxide or per-salt.

10. The method according to claim 9 wherein said peroxide is hydrogen peroxide.

11. A method for producing a composition comprising colloidal atomic nanosilver, comprising
    incubating, at a temperature from about 5° C. to about 45° C., probiotic bacteria that is a *Lactobacillus* species with an aqueous solution comprising
    a mixture of a silver salt; ammonia, an ammonium salt, or a combination thereof; and
    an alkali metal hydroxide;
    wherein the incubation time is from about 1 second to about 30 minutes; and
    wherein the incubation is performed at a pH within a range of from about 8 to about 12.

12. The method according to claim 11, wherein the amount of ammonia, ammonium salt, or mixture thereof is sufficient to form a $Ag(NH_3)^+$ or $\{Ag(NH_3)_2\}^+$ complex.

13. The method according to claim 11, wherein said alkali metal hydroxide is sodium hydroxide or potassium hydroxide.

14. The method according to claim 11, wherein the ratio of silver weight to cell dry weight of the bacteria is within a range from about 0.05 to about 20.

15. The method according to claim 11, wherein said silver salt is silver nitrate or silver chloride.

16. The method according to claim 11, further comprising removing at least part of said probiotic bacteria from the incubation mixture by means of mechanical, enzymatic, or physicochemical treatment.

17. The method according to claim 11, further comprising:
    centrifuging the incubation mixture into a solid portion comprising the composition having colloidal atomic nanosilver and a liquid portion, and
    separating said solid portion from the liquid portion.

18. The method according to claim 11, further comprising treating said composition comprising colloidal atomic nanosilver with a peroxide or per-salt.

19. The method according to claim 18 wherein said peroxide is hydrogen peroxide.

* * * * *

UNITED STATES PATENT AND TRADEMARK OFFICE
CERTIFICATE OF CORRECTION

PATENT NO. : 8,455,226 B2
APPLICATION NO. : 12/307190
DATED : June 4, 2013
INVENTOR(S) : De Windt et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 900 days.

Signed and Sealed this
Eighth Day of September, 2015

Michelle K. Lee
*Director of the United States Patent and Trademark Office*